(12) United States Patent
Jaffrey

(10) Patent No.: US 7,674,766 B2
(45) Date of Patent: Mar. 9, 2010

(54) MASS SPECTROMETRY-BASED IDENTIFICATION OF PROTEINS

(75) Inventor: Samie R. Jaffrey, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 387 days.

(21) Appl. No.: 11/057,082

(22) Filed: Feb. 11, 2005

(65) Prior Publication Data

US 2005/0277131 A1 Dec. 15, 2005

Related U.S. Application Data

(63) Continuation-in-part of application No. PCT/US03/24936, filed on Aug. 7, 2003.

(60) Provisional application No. 60/402,774, filed on Aug. 12, 2002.

(51) Int. Cl.
*A01N 37/18* (2006.01)
*A61K 38/00* (2006.01)
*C12Q 1/68* (2006.01)
*C12P 21/06* (2006.01)

(52) U.S. Cl. .............................. 514/2; 435/7.5; 435/68.1

(58) Field of Classification Search ....................... None
See application file for complete search history.

(56) References Cited

U.S. PATENT DOCUMENTS 5,408,038 A * 4/1995 Smith et al. .................. 530/359
6,379,971 B1 * 4/2002 Schneider et al. ............. 436/89
6,872,575 B2 * 3/2005 Regnier ....................... 436/174

OTHER PUBLICATIONS

Berne et al. Carboxypeptidase Y-Catalyzed Transpeptidation of Esterified Oligo- and Polypeptides and Its Use for the Specific Carboxyl-Terminal Labeling of Proteins. JACS 1992, vol. 114, pp. 2603-2610.*
Olejnik et al. Photocleavable biotin derivatives: A versatile approach for the isolation of biomolecules. PNAS. 1995. vol. 92, pp. 7590-7594.*
Carles et al. C-terminal labelling of B-casein. FEBS Letters. 1987. vol. 212, No. 1, pp. 163-167.*
Thiede et al. C-terminal ladder sequencing by an approach combining chemical degradation with analysis by matrix-assisted-laser-desorption ionization mass spectrometry. Eur. J. Biochem. 1977. vol. 244, pp. 750-754.*
Stennicke et al. C-Terminal Incorporation of Fluorogenic and Affinity Labels Using Wild-Type and Mutagenized Carboxypeptidase Y. Analytical Biochemistry. 1997. vol. 248, pp. 141-148.*
Righetti et al. Capillary electrophoresis of peptides and proteins in acidic, isoelectric buffers: recent developments. 1999. J. Biochem Biophys. Methods vol. 40, pp. 1-15.*
Hofmann et al. An approach to the targeted attachment of peptides and proteins to solid supports. PNAS. 1976. vol. 73, No. 10, pp. 3516-3518.*
Berne, P. , et al., "Peptide and Protein Carboxyl-Terminal Labeling Through Carboxypeptidase Y-Catalyzed Transpeptidation", *The Journal of Biological Chemistry*, 265, (Nov. 15, 1990), 19551-19559.
Flory, M. R., et al., "Advances in Quantitative Proteomics Using Stable Isotope Tags", *Trends in Biotechnology*, 20, (Dec. 1, 2002),S23-S29.
Geahlen, R. L., et al., "A General Method for Preparation of Peptides Biotinylated at the Carboxy Terminus", *Analytical Biochemistry*, 202, (1992),68-70.
Gygi, S. P., et al., "Quantitative Analysis of Complex Protein Mixtures Using Isotope-Coded Affinity Tags", *Nature Biotechnology*, 7 (Oct. 1999),994-999.
Lin, S. , et al., "C-Terminal Labeling of Immunoglobulin G with a Cysteine Derivative by Carboxypeptidase Y Catalyzed", *Analytical Biochemistry*, 285, (2000), 127-134.
Moseley, M. A., "Current Trends in Differential Expression Proteomics: Isotopically Coded Tags", *Trends in Biotechnology*, 19 (Oct. 2001),S10-S16.
Olejnik, J. S., et al., "Photocleavable Biotin Derivatives: a Versatile Approach for the Isolation of Biomolecules", *Proc. Natl. Acad. Sci. USA*, 92, (Aug. 1995),7590-7594.
Pan Dori, M. W., et al., "Photochemical Control of the Infectivity of Adenoviral Vectors Using a Novel Photocleavable Biotinylation Reagent", *Chemistry and Biology*, 9, (May, 2002),567-573.
Patton, W. F., "Detection Technologies in Proteome Analysis", *Journal of Chromatography B*, 771, Issues 1-2,(May 5, 2002),3-31.
Smolka, M. B., et al., "Optimization of the Isotope-Coded Affinity Tag-Labeling Procedure for Quantitative Proteome Analysis", *Analytical Biochemistry*, 297, (2001),25-31.

* cited by examiner

*Primary Examiner*—Cecilia Tsang
*Assistant Examiner*—Marcela M Cordero Garcia
(74) *Attorney, Agent, or Firm*—Schwegman, Lundberg & Woessner, P.A.

(57) ABSTRACT

The invention provides a method to C-terminally label proteins in a complex sample and identify those proteins, e.g., using mass spectrometry.

33 Claims, 8 Drawing Sheets

Biocytin derivative:

Blot: anti-biotin

Blot: anti-biotin

Preincubation time (pH 10.5)

Blot: anti-biotin

Blot: anti-biotin

MASS SPECTROMETRY-BASED IDENTIFICATION OF PROTEINS

RELATED APPLICATIONS

This application is a continuation-in-part under 35 U.S.C. § 111(a) of International Application No. PCT/US03/24936 filed Aug. 7, 2003 and published in English as WO 2004/015391 on Feb. 19, 2004, which claimed priority from Provisional Application No. 60/402,774, filed Aug. 12, 2002, which applications and publication are incorporated herein by reference.

BACKGROUND OF THE INVENTION

A major goal of preventive medicine is to diagnose diseases in which early intervention can alter the outcome of the disease. One example of such a disease is pancreatic cancer, a neoplasm which kills 24 000 people in the United States every year, and whose incidence has increased threefold in the last forty years (Brand 2001). Pancreatic cancer is highly fatal with only 10% of patients surviving one year past the time of diagnosis (Brand, 2001). An exception to this high mortality rate for pancreatic cancer is among patients in whom the cancer is detected early; in rare cases small carcinomas at the head of the pancreas are associated with hepatobiliary obstruction and painless jaundice, prompting radiographic studies that identify the cancer at an early, resectable stage (Brand, 2001). Thus, early detection of pancreatic cancer can have a major impact on the prognosis of the disease. Importantly, early detection of other cancers, such as cervical cancer by the Pap smear, and prostate cancer, with the PSA blood test, have had a substantial impact on the mortality of these diseases. Thus, early detection is a key strategy in the fight against cancer.

However, early detection does not have an impact solely on cancer. Other diseases, such as Parkinson's disease, can be ameliorated with early intervention. Patients with Parkinson's disease show delayed progression following treatment with monoamine oxidase inhibitors (Koller, 1997). Conceivably, early intervention of Parkinson's disease with this class of drugs can delay the onset of the characteristically debilitating tremor, muscle atrophy, and neurodegeneration associated with this disease.

Ten years ago, a major international effort was initiated to sequence the entire human genome, which amounts to 3.2 million basepairs. By mid-2000, a draft of the human genome was announced, comprising a majority of the coding sequences. With the completion of the sequencing of the genomes of yeast (Mewes et al., 1997), *Caenorhabditis elegans* (The *C. elegans* Sequencing Consortium, 1998), and *Drosphilia* (Adams et al., 2001), and the anticipation of the complete human genome being fully sequenced by 2003, there is no doubt that this vast set of knowledge will have a substantial impact on the diagnosis and treatment of human disease.

In particular, the sequencing of the human genome provides data that can be used to identify markers for early stages of disease, e.g., neoplastic and cardiovascular diseases. Once the identity of every protein in the human proteome is known, the levels of each protein can be individually queried in a systematic manner, and compared from blood samples of patients with the disease, and unafflicted patients. Epidemiological studies comparing large numbers of afflicted patients with unafflicted patients can lead to the identification of proteins whose expression level is increased or decreased only in the case of disease. These proteins can then be detected in routine blood assays in the general population, much in the same way that Caucasian men over 50 years and African-American men over 40 years take a yearly PSA blood test to screen for prostate cancer.

A number of methods have been developed to take advantage of the newly generated genomic data, most notably "gene-chip" technology, that provide a way to simultaneously quantitate transcript levels of numerous genes. While this method is useful, for most experimental purposes, quantitation of protein levels is more relevant than quantitation of transcript levels. Indeed, in many well-documented cases, changes in mRNA levels do not correlate linearly with changes in protein levels (Gygi et al., 1999; Anderson et al., 1997); moreover, the levels of some proteins are regulated at the level of protein stability. For example, the cell cycle is crucially dependent on the stability of cyclins, which are regulated by cell-stage-specific ubiquitination. Additionally, some samples, such as serum, which are particularly useful because they are easily collected from patients for diagnostic purposes, are composed of proteins whose transcripts reside in a variety of diverse tissues. Unfortunately, technology to assess protein levels is remarkably underdeveloped compared to DNA technologies.

The principle technique to study protein levels involves subjecting different samples to two-dimensional gel electrophoresis (2DE) and comparing the pattern of spots that arise following staining. The identities of spots with different intensities can be determined by excising the spot, trypsinizing the eluted protein, and subjecting the peptides to MALDI/MS. One major limitation of this approach is that only proteins that are excised from the gels are examined, leaving the identities of non-excised spots unknown. Another limitation is that many proteins, especially those which are highly charged or have transmembrane segments, resolve poorly on 2DE gels. Most importantly, since only a relatively small amount of protein can be loaded onto the gels, most proteins are present at levels below the level of detection by MALDI/MS.

Mass spectrometry (MS) is a technique that is capable of generating molecular weight data for peptides and other small molecules, and tandem mass spectrometry (MS/MS) is a technique that provides sequence information for peptides. Because full-length proteins do not produce highly accurate data by MS, samples are first digested with proteases, such as trypsin, and the resulting peptide mixture is subjected to MS and MS/MS. Using data from the completed genome sequencing projects, molecular masses and sequence information obtained by MS and MS/MS can be used to identify parent proteins that were present in the original samples.

Although an approach which employs MS is useful, the complexity of the peptide mixture increases as the number of proteins in the starting material is increased. For example, digestion of the yeast proteome, which comprises 6,000 proteins, results in 344,000 peptides. Peaks seen by MS analysis of these complex mixtures often cannot be interpreted because they represent numerous different peptides with similar molecular masses. Additionally, low abundance peptides are often invisible or lie within or adjacent to peaks of higher abundance. Typically, a liquid chromatography-electrospray mass spectrometer can resolve approximately 30,000 peptides (Gygi et al., 1999). Thus, because of the large number of peptides that would be generated, MS analysis does not appear to be feasible for higher eukaryotes using current technology.

Thus, there is a need for a method to simplify complex mixtures so that proteins in complex mixtures can be readily identified.

SUMMARY OF THE INVENTION

The invention provides a method which leads to the production of a single peptide per protein in a starting sample, e.g., a biological mixture, resulting in the maximal possible simplification of a peptide mixture. The method involves the incorporation of a label comprising an affinity marker at the C-terminus of each protein in a sample using the reverse reaction of a transpeptidase, e.g., a yeast exopeptidase such as carboxypeptidase Y (CPY), which preferably is specific for the C-terminus. Accordingly, protein mixtures are contacted with a transpeptidase under conditions which favor transpeptidase-mediated ligation of a label comprising an affinity marker, e.g., biotin or biocytin-$NH_2$, to each protein resulting in C-terminal labeling of each protein. As used herein, the term "label" refers to a molecule comprising an affinity marker, which is detectable or capable of detection, however, the term "affinity marker" does not include a natural amino acid. In one embodiment of the invention, the label comprises a photocleavable affinity marker, such as photocleavable biotin, which allows labeled peptides to be selectively eluted from a ligand for the affinity marker, e.g., from avidin supports with 300-350 nm illumination, as illumination results in cleavage of the peptides from the ligand-bound affinity marker, resulting in elution of peptides that no longer have the affinity marker. In addition to the affinity marker, the label may further comprise an amino acid moiety or a derivative thereof (e.g., an amidated amino acid moiety, such as the amidated lysine moiety of biocytin amide), and/or a non-natural isotope. A "non-natural isotope" as used herein refers to an isotope that is not the predominant isotope for its element, e.g., deuterium, $^{13}C$ or $^{15}N$.

C-terminally labeled proteins are then hydrolysed either chemically or with a protease such as trypsin to generate a mixture of peptides including C-terminally labeled peptides. Preferably, the proteins are cleaved at specific residues, e.g., by a specific protease such as trypsin, endoprotease Glu-C or endoprotease Arg-C. The C-terminal peptides are then isolated using a ligand for the affinity marker, e.g., streptavidin-agarose. In one embodiment, the isolated peptides are collected and separated by MS, and, optionally, identified, e.g., by sequence analysis. As used herein "identify" refers to characterizing a peptide by its molecular weight, amino acid composition and/or amino acid sequence. The identified peptides may then be correlated to a protein which was present in the sample. In one embodiment, prior to MS, the labeled peptides are fractionated. Fractionation can be by, for instance, any type of chromatography or electrophoresis, including but not limited to reverse phase HPLC, ion exchange chromatography, capillary electrophoresis, or a combination thereof.

The ability to label the C-terminus of proteins thus provides a straightforward way to perform proteome analysis and so the method of the invention overcomes the limitations of current proteomic approaches and can be employed with MS-based approaches for highly complex mammalian proteomes. MPACT can be used to profile protein expression in any sample, e.g., in sarcoplasmic reticulum derived from normal and chronic heart failure (CHF) patients, or a plurality of samples to identify protein changes associated with a particular disease or condition, e.g., CHF and its reversal by LVAD therapy, or associated with treatment with an exogenous agent(s). Moreover, MPACT can be used with whole tissue, e.g., cardiac tissue samples, to characterize, at a systems level, protein and to identify prognostic markers for particular conditions. A combined multidimensional LC-MS/MS and MPACT approach can also be employed to profile protein expression in cardiac tissue to assess protein expression changes in vascular cells, hearts from animal models of septic shock and ischemia-reperfusion injury, as well as cardiac tissue from CHF patients before and after LVAD therapy.

DETAILED DESCRIPTION OF THE INVENTION

Figure 1:
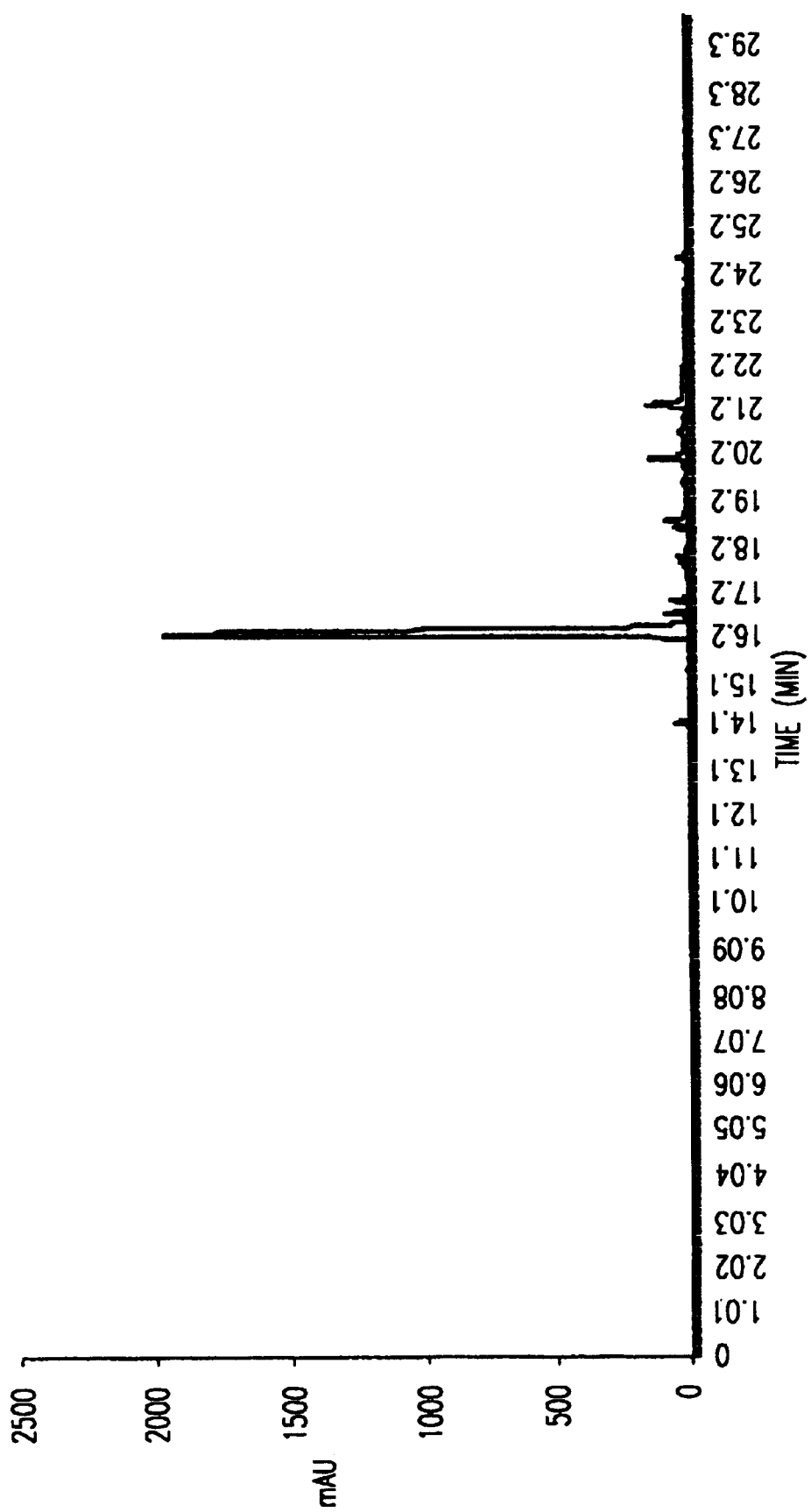
FIG. 1 depicts a HPLC analysis of Fmoc-Lys-$NH_2$.

The invention provides a method which leads to the production of a single peptide per protein in a starting sample, e.g., a biological mixture, resulting in the maximal possible simplification of a peptide mixture. The method involves the incorporation of a label comprising an affinity marker at the C-terminus of each protein in a sample using the reverse reaction of a transpeptidase, which preferably is specific for the C-terminus. Accordingly, protein mixtures are contacted with a transpeptidase under conditions which favor transpeptidase-mediated ligation of a label comprising an affinity marker, e.g., biotin or biocytin-$NH_2$, to each protein resulting in C-terminal labeling of each protein. In addition to the affinity marker, the label may further comprise an amino acid moiety or a derivative thereof (e.g., an amidated amino acid moiety, such as the amidated lysine moiety of biocytin amide), and/or a non-natural isotope.

C-terminally labeled proteins are then hydrolysed either chemically or with a protease such as trypsin to generate a mixture of peptides including C-terminally labeled peptides. The C-terminal peptides are then isolated using a ligand for the affinity marker, e.g., streptavidin-agarose. In one embodiment, the isolated peptides are collected and separated by MS, and, optionally, identified, e.g., by sequence analysis. The identified peptides may then be correlated to a protein which was present in the sample. In one embodiment, prior to MS, the labeled peptides are fractionated. Fractionation can be by, for instance, any type of chromatography or electrophoresis, including but not limited to reverse phase HPLC, ion exchange chromatography, capillary electrophoresis, or a combination thereof.

Isotope-coded affinity tags (ICAT) reagents, which are used for global quantitative proteome analysis, suffer from several problems that limit the utility of the ICAT technique (Gygi et al., 1999). These limitations include (1) copurification of spurious, non-labeled peptides following elution of ICAT-labeled peptides from monomeric avidin; (2) the presence of a large biotin adduct which complicates CID fragmentation spectra interpretation; (3) unequal retention times of heavy and light ICAT reagents on RP-HPLC resulting in heavy and light peptides not being ionized in the MS source simultaneously; and (4) nonspecific reactivity of ICAT reagents with noncysteine nucleophiles in proteins. In contrast, the C-terminal origin of each peptide prepared by the methods of the invention provides a powerful constraint when its identity is determined, making CID mass spectra interpretation substantially simpler and more reliable. This constraint may make it possible to identify the parent protein based solely on the molecular weight of the peptide. Thus, the mass of a peptide would be compared to the predicted molecular weights of all C-terminal peptides in a given species' proteome. In cases where the abundance of the peptide is too low to obtain fragmentation data, using the mass of the peptide to identify the parent protein substantially improves the sensitivity compared to approaches, such as ICAT, in which CID mass spectra is essential for peptide identification.

The methods of the invention are particularly useful to compare the expression levels of large numbers of proteins derived from two different samples e.g., two different cellular sources or tissues, for example, samples differentially exposed to an agent, using electrospray ionization mass spectrometry. In order to perform comparative MPACT, two or more samples are distinguished based on the corresponding C-terminus of the proteins in each sample. For instance, the label for one sample comprises an affinity marker and a non-natural isotope, e.g., a deuterated tag, $^{13}C$ or $^{15}N$, while the label for the other sample comprises the affinity marker but does not comprise the non-natural isotope.

In one embodiment of the invention, the method is employed to detect proteins whose expression level is up- or down-regulated in comparison to control environments. Samples of proteins from control and experimental conditions (e.g., from cells contacted with a drug) are obtained. Proteins in one sample are C-terminally labeled with a label which does not comprise a non-natural isotope. Proteins in the other sample are C-terminally labeled with a label comprising one or more non-natural isotopes. In one embodiment, the two labeled samples are mixed prior to hydrolysis. After hydrolysis, e.g., with a protease, the C-terminally labeled peptides or C-terminal peptides, obtained by removing the affinity marker from the terminally labeled peptides, are purified, and the purified peptides are subjected to analysis by MS. Preferably, before analysis by MS, the labeled peptides are fractionated. Fractionation can be by, for instance, any type of chromatography or electrophoresis. Most commonly, fractionation is accomplished by reverse phase HPLC, ion exchange chromatography, or capillary electrophoresis. Ideally, the majority of labeled peptides in one sample are chemically equivalent but isotopically distinct from the labeled peptides in the other sample. In this context, chemical equivalence is defined by substantially identical chromatographic or electrophoretic behavior during the fractionation step. Corresponding C-terminal peptides of the two samples will differ in mass by the difference in mass of the labels for the two samples. The relative amounts of the corresponding peptides can be determined by the ratio of their peak height or area in MS. For example, most pairs of corresponding peptides will have the same ratio of peak height or area in MS. Those with a different ratio, it can be concluded, are derived from proteins that are up- or down-regulated in the experimental sample relative to the control.

The invention will be further described by the following non-limiting examples.

EXAMPLE 1

Synthesis and Purification of Nα-Fmoc-Lys-NH$_2$

Step 1: Synthesis of Nα-Fmoc-Lys-NH$_2$

Nα-Fmoc-Lys-NH$_2$ is used to synthesize PCB-NH$_2$. The presence of the Fmoc protecting group allows PCB-NH$_2$ to react with the Nε of Lys instead of Nα.

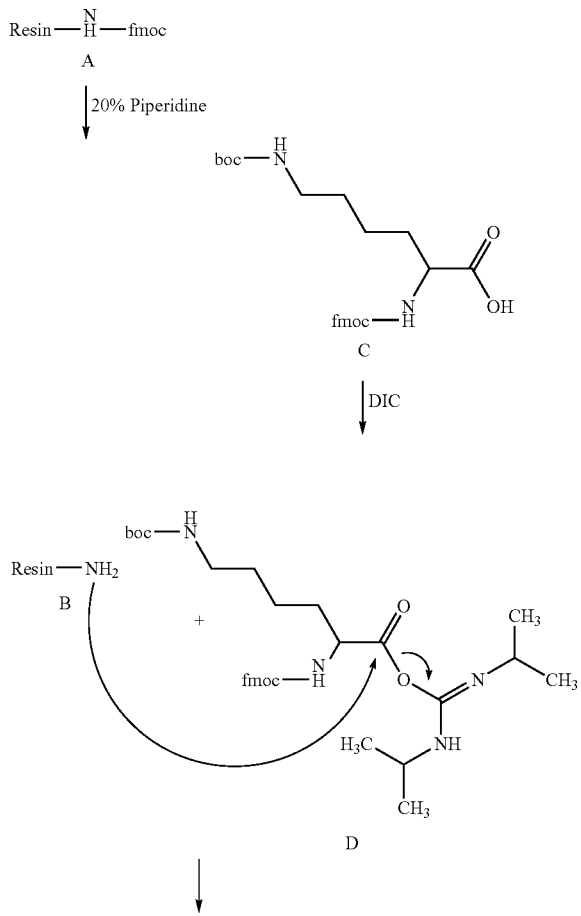

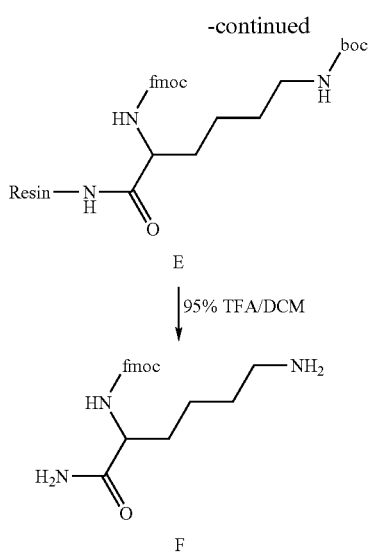

A. NHS-PC-LC Biotin coupling reaction with Fmoc-Lys-NH₂.
B. Fmoc-PCB-NH₂
C. PCB-NH₂

Method

1. Removal of Fmoc from Knorr Resin
   a. Place 125 mg (capacity=0.1 mmole) of Knorr Resin (Advanced ChemTech) into a 10 mL peptide synthesis vessel.
   b. Turn the stopcock of the vessel to the closed position.
   c. Add 1.25 mL of 20% piperidine/DMF.
   d. Slowly bubble $N_2$ through to agitate the mixture for 30 minutes at RT.
   e. Vacuum-filter the resin and wash three times with 5 mL DMF.

2. Attachment of Nα-Fmoc-Nε-Boc-Lys to the Resin
   a. Suspend the resin in 1.875 mL of DMF in peptide synthesis vessel.
   b. Slowly bubble $N_2$ through.
   c. Prepare lysine solution:
      i. In a 20 mL vial, dissolve 117 mg (0.25 mmole) of Nα-Fmoc-Nε-Boc-Lys (Sigma) in 3 mL of DMF.
      ii. Add 47.2 mg (0.35 mmole) of hydroxybenzotriazole (ICN).
      iii. Tap the bottom of the vial until HOBt is completely dissolved.
      iv. Add 39.1 μL (0.25 mmole) of diisopropylcarbodiimide (Sigma).
      v. Incubate for 10 minutes at room temperature.
   d. Add lysine solution to resin.
   e. Allow the reaction to proceed, with nitrogen bubbling through, for 3 hours at room temperature.

3. Blocking of Unreacted Resin (Optional)
   a. Add 18.9 μL of acetic anhydride (0.2 mmole) to the reaction vessel.
   b. Add 16.2 μL of pyridine (0.1 mmole).
   c. Allow blocking reaction to proceed for 30 minutes at room temperature.

4. Cleavage of Nα-Fmoc-Lys-NH₂
   a. Once the blocking reaction is completed, drain the solvent by vacuum filtration.
   b. Wash the resin three times with 5 mL of DMF.
   c. Wash the resin three times with 5 mL DCM.
   d. Turn the nitrogen off.
   e. Add 3-5 mL of 95% TFA/DCM.
   f. Allow the mixture to stand in RT for 30 minutes.
   g. Filter and wash the resin with 5 mL of DCM.
   h. Combine the filtrate.

Step II. Purification of Nα-Fmoc-Lys-NH₂

1. Vacuum-dry the filtrate to obtain red sticky tar.
2. Add 10-15 mL of cold (−20° C.) ether to the dried sample. Red tar becomes white/ivory.
3. Incubate the sample at −20° C. for 30 minutes.
4. Transfer the mixture into a 50 mL conical.
5. Spin the mixture at 3K rpm for 10 minutes.
6. Pipet away the supernatant.
7. Wash the precipitant with cold ether.
8. Repeat steps 5 through 7 twice.
9. Transfer the mixture to a scintillation vial.
10. Dry off the ether using speedvac.
11. Store the product dry at −20° C.
    a. HPLC parameters
       i. Flow: 4 mL/minutes
       ii. UV: 280 nm
       iii. Inject: 100 μL
       iv. Gradient
       1. 0% D and 100% A (t=0 minutes)
       2. 0% D and 100% A (t=5 minutes)
       3. 100% D and 100% A (t=25 minutes)
       4. 100% D and 100% A (t=30 minutes)
          A=0.1% TFA/H₂O
          A=95% ACN, 0.1% TFA, 4.9% H₂O FIG. 1 is a purity analysis of Fmoc-Lys-NH₂ by HPLC. 2 mg of Fmoc-Lys-NH₂ was dissolved in 300 μL of water. To prepare the sample for HPLC, particulate materials were removed by spinning down the sample at 14 k rpm for 5 minutes. 10 μL of supernatant was injected to HPLC, 9.4×250 mm C-18 semi-prep column (5 μm).

EXAMPLE 2

Synthesis and Purification of Photocleavable Biocytinamide (PCB-NH₂)

Step I: Synthesis of PCB-NH₂

PCB-NH₂ is a molecule which can be used in CPY-dependent C-terminal labeling reaction which reaction products can release protein-Lys-NH₂ when irradiated with UV light (300-360 nm) and so PCB-NH₂ is a useful reagent in purifying peptides and/or proteins. PCB-NH₂ can be synthesized from NHS-PC-LC-Biotin (Pierce, 21332) and Fmoc-Lys-NH₂, and the product purified by HPLC.

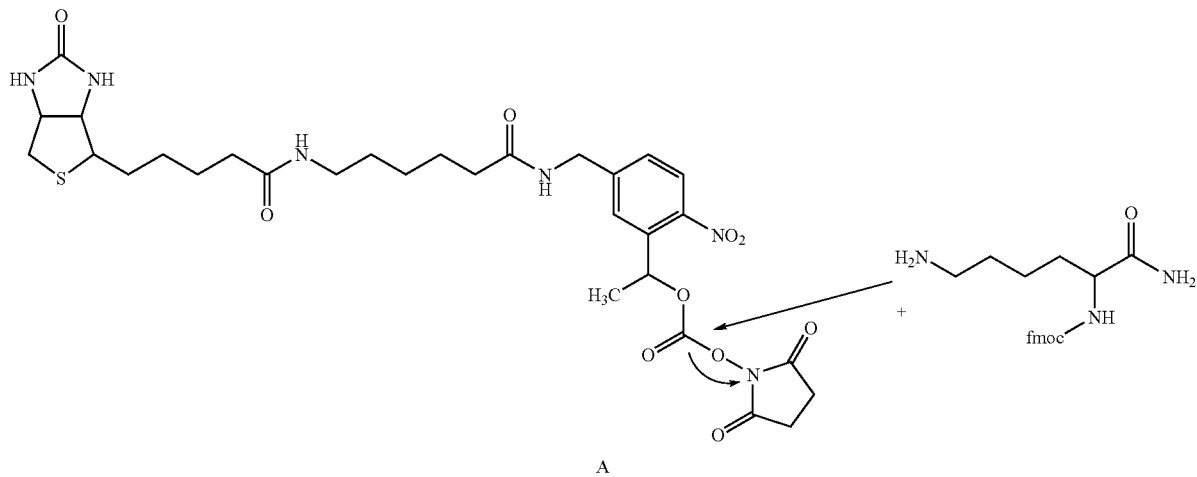
A
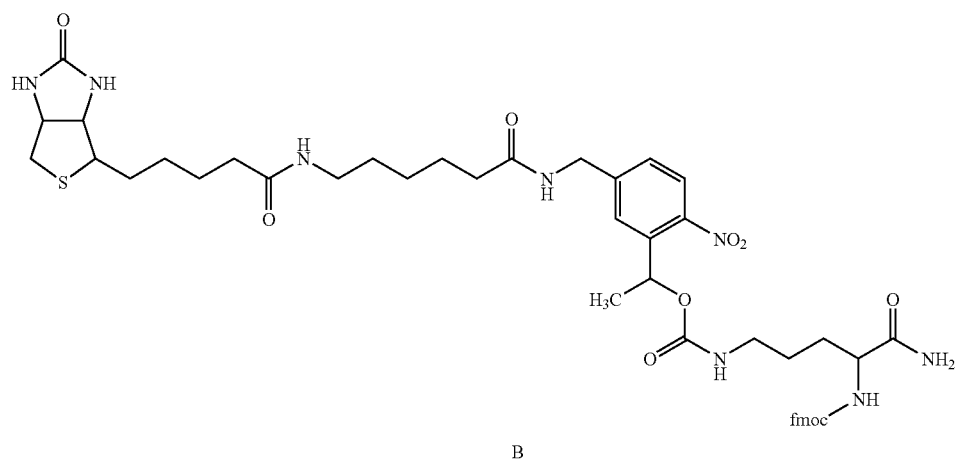
B
20% Piperidine/DMF
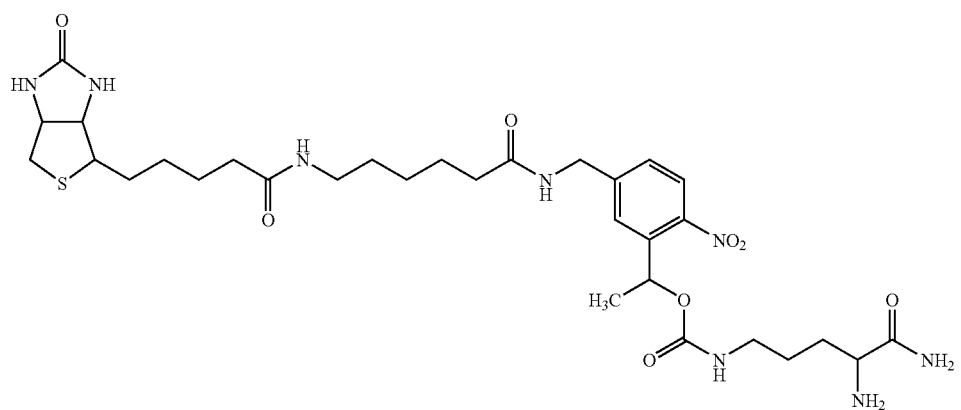
C

A. NHS-PC-LC Biotin coupling reaction with Fmoc-Lys-NH$_2$

B. Fmoc-PCB-NH$_2$

C. PCB-NH$_2$

Methods

1. NHS-PC-LC-Biotin Solution (MW=676.74) (Avoid Light Exposure)
    a. Dissolve 2 mg (3.0 μmoles) of NHS-PC-LC Biotin (Pierce, #21332) in 40 μL of DMF.
    b. Add 6.28 μL (45 μmoles) of TEA (EM Sciences)

2. Fmoc-Lys-NH$_2$ Solution (MW=367.45)
    a. Dissolve 5.9 mg (16 μmoles) of Fmoc-Lys-NH$_2$ (synthesized in the lab) in 233 μl of DMF.

3. Reaction (Avoid Light Exposure)
    a. Put 40 μL of NHS-PC-LC-Biotin solution in a 1.5 mL microcentrifuge tube.
    b. Add 233 μL of Fmoc-Lys-NH$_2$ solution (drop wise, over 2 minutes, with trituration) to NHS-PC-LC-Biotin solution.
    c. Allow the reaction to proceed for 2-3 hours at room temperature, in the dark.

Step II: Purification of Fmoc-PCB-NH$_2$

1. To prepare the sample for HPLC, remove particulate materials by spinning down the synthesis product at 14,000 rpm for 5 minutes.
2. Take 100 μL of supernatant and run it on HPLC, C-18 semi-prep column (9.4×250 mm; 5 μm).
    a. HPLC parameters
        i. Flow: 4 mL/minute
        ii. UV: 280 nm
        iii. Inject: 100 μL
        iv. Gradient
            1. 0% D and 100% A (t=0 minutes)
            2. 0% D and 100% A (t=5 minutes)
            3. 100% D and 100% A (t=25 minutes)
            4. 100% D and 100% A (t=30 minutes)
                A=0.1% Formic Acid/H$_2$O
                D=95% ACN/0.1% Formic Acid/H$_2$O
3. Turn off the UV at 18.6 minutes to prevent photolysis of the compound.
4. Collect the fraction from 18.7 minutes to 19.8 minutes in a 20 mL scintillation vial covered with aluminum foil.
5. Repeat the HPLC run twice more to purify the entire sample.
6. Dry down the purified sample using Speedvac at 4° C. overnight.

Figure 2:
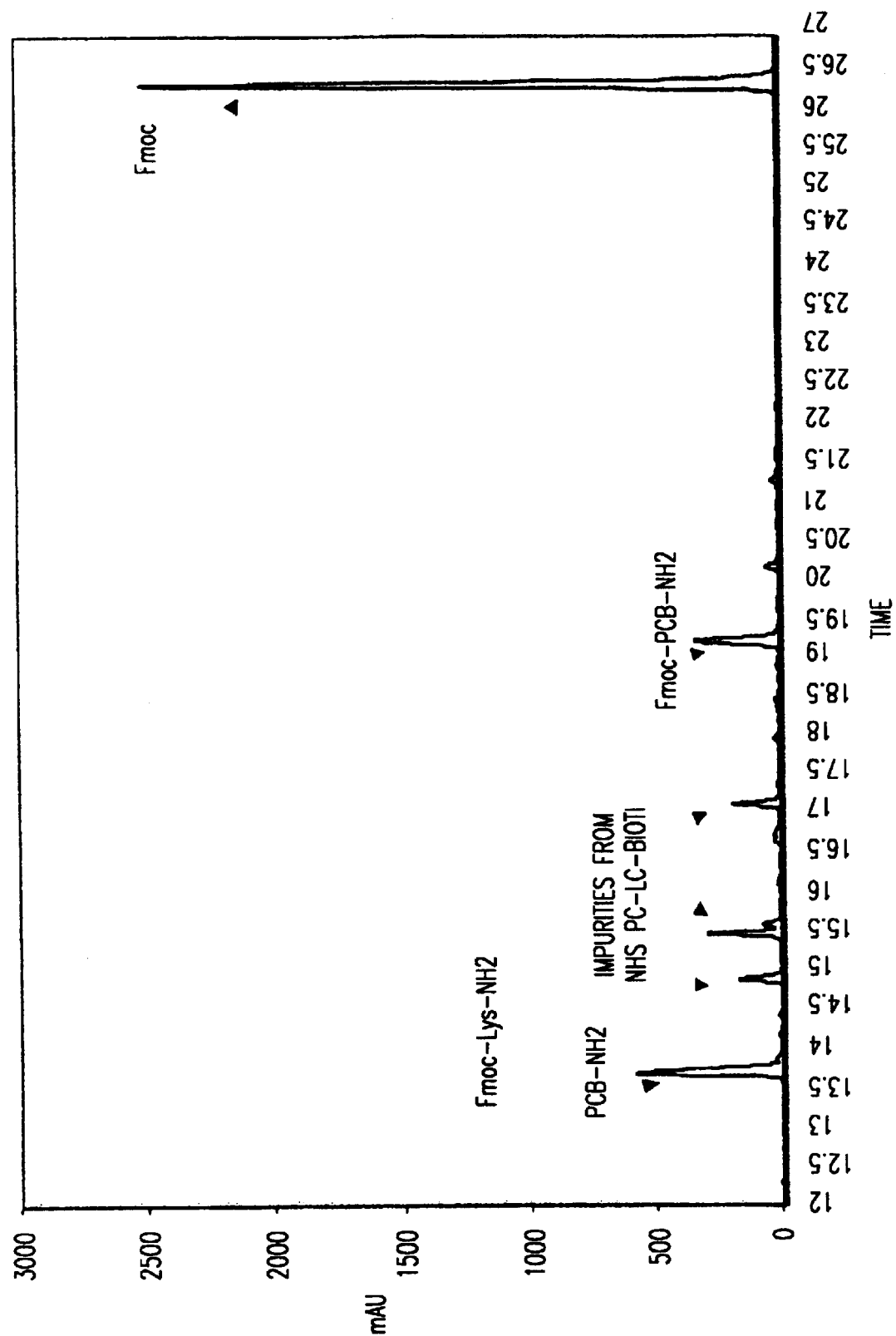
FIG. 2 depicts a HPLC analysis of Fmoc-PCB-$NH_2$ synthesis.

HPLC analysis of Fmoc-PCB-NH$_2$ is shown in FIG. 2. The fraction at 19.3 minutes corresponds to Fmoc-PCB-NH$_2$, and the fraction at 13.7 minutes corresponds to PCB-NH$_2$. The photocleavable biotin may attach to either Nα or Nε of Lys-NH$_2$.

Step III. Deprotection of Fmoc-PCB-NH$_2$

Methods

1. Dissolve 0.5 mg (0.7 μl) of Fmoc-PCB-NH$_2$ in 400 μL of DMF.
2. Add 100 μL of piperidine (Sigma) to make 20% piperidine/DMF solution.
3. Incubate for 30 minutes at room temperature.
4. Add 42.5 μL of formic acid (ICN) to neutralize piperidine.
5. To prepare the sample for HPLC, remove particulate materials by spinning down the synthesis product at 14,000 rpm for 5 minutes.
6. Take 100 μL of supernatant and run it on HPLC, C-18 semi-prep column (9.4×250 mm; 5 μm).
    a. HPLC parameters
        i. Flow: 4 mL/minute
        ii. UV: 280 nm
        iii. Inject: 100 μL
        iv. Gradient:
            1. 0% D and 100% A (t=0 minutes)
            2. 0% D and 100% A (t=5 minutes)
            3. 100% D and 0% A (t=25 minutes)
            4. 100% D and 0% A (t=30 minutes)
                A=0.1% Formic Acid/H$_2$O
                D=95% ACN/0.1% Formic Acid/H$_2$O
7. Turn off the UV at 14.2 minutes to prevent photolysis of the compound.
8. Collect the fraction from 14.3 minutes to 15.3 minutes in to 20 mL scintillation vial covered with aluminum foil.
9. Repeat the HPLC run four times more to purify the entire sample.
10. Dry down the purified sample using Speedvac at 4° C. overnight.

Deprotection of Fmoc may also be conducted immediately after the synthesis.

Figure 3:
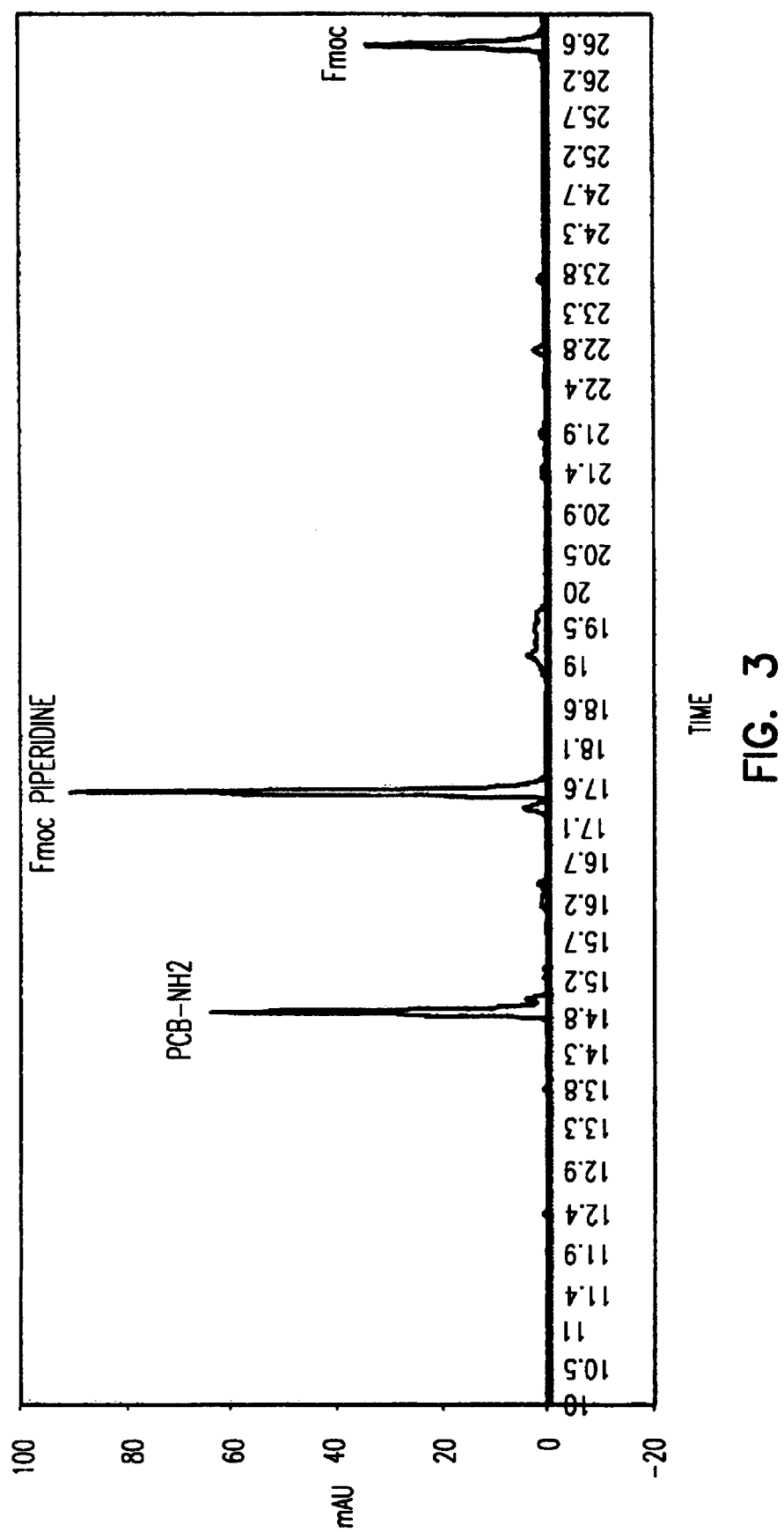
FIG. 3 illustrates a HPLC analysis of the deprotection of Fmoc-PCB-$NH_2$.

FIG. 3 shows the deprotection of Fmoc-PCB-NH$_2$.

EXAMPLE 3

Preparation of C-terminally Labeled Peptides using PCB-NH$_2$

1. Protein Methyl Esterification.
    Make 25 mM HCl solution in methanol.
        Use concentrated HCl to minimize H$_2$O in sample.
    Dissolve 5 mg of protein in 1 mL of 25 mM HCl/MeOH
    Incubate at the protein solution at 4° C. on a rocking platform for 48 to 72 hours.

2. Removal of MeOH.
    Make 25 mM NaOAc/H$_2$O from a 3 M stock, pH 5.2
        Samples incubated less than 48 hours or more than 72 hours produced less biotinylated BSA signals on Western blots.
    Add 1 mL of 25 mM NaOAc solution to 1 mL of protein methyl ester sample (from step #1)
    Rotary-evaporate the above solution to remove methanol (The final volume should be 1 mL)
        Since the pump pulls relatively strong vacuum and methanol is very volatile, place the reaction flask in ice water bath.
        Place the collecting flask in ice.
        BSA-methyl-ester produced less biotinylated BSA signals when sulfuric acid was used instead of hydrochloric acid. This effect was seen only when rotary evaporation was used to remove methanol from the sample. This effect was not seen when acetone precipitation was used.

3. CPY Labeling (Performed in the Dark)
    Make stock solution of 5.4 mM PCB-NH$_2$ in H$_2$O.
    Make 1 M Na$_2$CO$_3$ fresh, 2 mg of CPY in 1 mL of 1:1 PBS:Glycerol, and 20% Triton X-100.
    Keep all the samples/reaction mixtures in ice.
        Stock CPY solution is diluted 10× with 1:1 PBS:Glycerol. 10% stock has been found to produce better labeling.
        The enzymatic activity of CPY in PBS Glycerol solution did not diminish even after two months in 4° C.

Make batch solution (for 75 μL of methanol-free protein-methyl ester) of Na$_2$CO$_3$, TritonX-100, and PCB-NH$_2$
  Put 7.5 μL of 1 M Na$_2$CO$_3$, 7.5 μL of 20% TritonX-100, and 70 μL of 5.4 mM PCB-NH$_2$/H$_2$O into an eppendorf tube. Triturate the solution.
Put 8.5 μL of batch solution to the bottom of an eppendorf tube.
Put 7.5 μL of rotary vaporized protein methyl ester solution (from step #2) onto the inside of the cap of the eppendorf tube.
Put 1 μL of 10% CPY reagent on the inside wall of the eppendorf tube.
  This order of addition keeps CPY and protein-methyl ester from the harsh basic condition of sodium carbonate until the reaction/incubation.
Spin the samples (3000 rpm for 15 seconds)
Tap the bottom of the eppendorf tube to mix the reagents. Spin the tubes again.
Add 0.42 μL of 20% SDS to make 0.4-0.5% SDS solution.
  To avoid pipetting less than 1 μL, prepare samples in large volumes 10× or larger.
  SDS concentration less than 0.4% causes precipitation.
  Keeping SDS containing sample in ice causes precipitation.
Furthermore, addition of SDS to cold sample causes precipitation.
Incubate the tube in 37° C. for 20 minutes.
  Time course experiment of CPY labeling reaction showed 20 minutes of incubation to be the optimal incubation time.
    volumes indicated in this section are designed for one sample on a SDS-PAGE.

4. Isolation of Biotinylated BSA
  Put the reaction mixture from step #3 into a 10,000 MW, Pierce Slide-A-Lyzer cassette.
    It took roughly 4 hours for 500 μL BSA sample (10 mg/mL BSA, 0.2% SDS, 100 mM NaCl, 50 mM Hepes pH 7.7, 5 mM B-NH$_2$) to lose about 99% of PCB-NH$_2$ into 500 μL of PBS.
    4° C. dialysis of biotinylated BSA in CPY reaction mixture showed 6 hour dialysis as preferred dialysis period.
  Dialyze each cassette against 3 L of PBS in cold room for 6 hours. Repeat this dialysis for 4 cycles. (Collect 10 μL sample for TLC analysis, using fluorescamine to detect free amines on PCB-NH$_2$, at the end of each cycle).

5. Trypsinization of Biotinylated Protein
  Dissolve 4.2 mg of trypsin (Sigma T-8802) in 5.6 mL of cold 50 mM Hepes, pH 7.7.
    Keep trypsin in ice to minimize the loss enzymatic activity of trypsin.
  Dilute above trypsin solution by 10 times, with 50 mM Hepes pH 7.7, to obtain 5% (mass ratio against protein-methyl ester) trypsin solution.
  Incubate dialyzed, biotinylated proteins (from step #4) with 5% trypsin at 37° C. overnight. (The volume ratio between protein sample and 5% trypsin is 17:50).
    5% trypsin (relative to substrate mass) produces enhanced digestion of biotinylated BSA.

6. Inactivation of Trypsin
  Pack NeutrAvidin resin on a fritted column.
    NeutrAvidin resin has binding capacity of 20 μg or 82 nmoles of Biotin/mL of resin.
    Experiments with pyruvate carboxylase showed NeutrAvidin resin captures more biotinylated molecules when multiple column loading (10 times or more reloading) was used rather than 1-2 hours of batch loading.
  Equilibrate the resin with 10× the resin volume of 50 mM Hepes pH 7.7. Repeat 3 times.
  Load the sample.
  Collect the flow through and reload onto the column.
  Repeat the reloading step 20 times.
  Wash the resin with 10× the resin volume of 50 mM Hepes pH 7.7 three times.
  Wash the resin the 10× the resin volume of 50 mM Hepes pH 7.7 that has 1 M NaCl.
  Wash the resin with 10× the resin volume of 50 mM Hepes pH 7.7.
  Wash the resin with 10× the resin volume of 1 M Guanidine HCl/100 mM Hepes pH 7.7.
  Wash the resin with 10× the resin volume of 50 mM Hepes pH 7.7.
  Wash the resin with 10× the resin volume of H$_2$O three times.
  Resuspend the resin in 3× the resin volume of 50 mM Hepes pH 7.7.
  Transfer the resin and the 50 mM Hepes pH 7.7 solution to a quartz cuvet.
  Irradiate the cuvet for 2 hrs with 365 run UV lamp while gently mixing the solution.
  Transfer the resin and the 50 mM Hepes pH 7.7 solution to an eppendorf tube.
  Spin the resin down and collect the supernatant.
  Resuspend the resin with 2× the resin volume of 50 mM Hepes 7.7 and spin down the resin. Collect the supernatant.

8. Removal of Salts from the Peptide Solution
  Condition the Waters OASIS HLB 1 cc Extraction Cartridge with 1 mL of acetonitrile.
  Equilibrate the column with 1 mL H$_2$O twice. Use a syringe and a reservoir adapter (Waters) to force the liquid down.
  Load the sample (from step #7).
  Wash the column with 1 mL of H$_2$O four times. Use a syringe and a reservoir adapter (Waters) to force the liquid down.
  Elute the sample in 1 mL of 0.1% TFA in acetonitrile.
  Collect the eluate and elute with another 1 mL of 0.1% TFA in acetonitrile.
  Dry down the eluate in speedvac at 4° C.

9. Purification of Peptides
  Resuspend the dried down sample in minimal ACN (usually 20-30 μL)
  Dilute the sample with water. Reduce the ACN concentration down to 10% or less.
  To prepare the sample for HPLC, remove particulate materials by spinning down the sample at 14 k RPM for 5 minutes.
  HPLC purify the peptides
    HPLC parameters
      1. UV: 20
      2. Flow: 4 mL/minute
      3. Column: C-18 Semi-Prep 9.6×250 mm (5 μm)
      4. Gradient (A=0.1% TFA/H$_2$O D=95% ACN, 0.1% TFA, 4.9% H$_2$O)
        a. 0% D and 100% A at t=0 minutes
        b. 0% D and 100% A at t=5 minutes
        c. 100% D and 0% A at t=25 minutes
        d. 100% D and 0% A at t=30 minutes Collect peptide fractions in tared glass vials and dry them down.

Weigh the vials that contain dry samples.

Calculate the number of moles in the sample.

Redissolve the samples in ACN.

10. Analyze the sample using MALDI.

EXAMPLE 4

Mass Spectrometric Proteome Analysis with C-terminal Tags (MPACT)

A peptide mixture obtained from the trypsinization of a protein mixture could be maximally simplified if just one peptide was recovered for each protein in the starting material. If each protein in the starting material could be modified with a single label, the digested protein would produce several peptides, only one of which would possess the label, and the label could then be used to retrieve the single peptide. One approach would be to label one end of the protein, for example, the C-terminus. The incorporated label could be biotin because modified proteins could be detected by Western blotting with biotin-specific antibodies and streptavidin-agarose provides a way to recover the labeled proteins.

Figure 4:
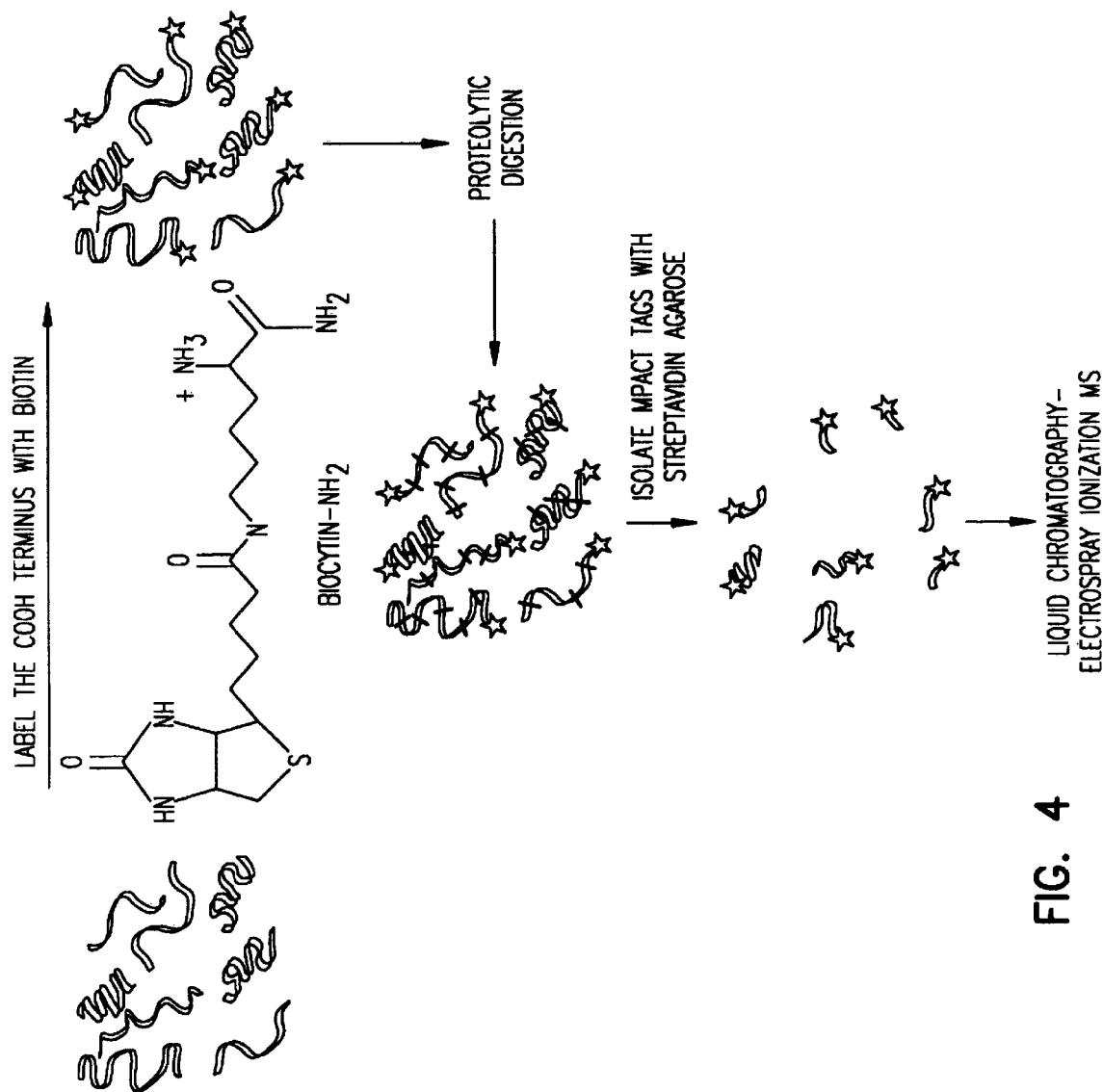
FIG. 4 is a schematic of mass spectrometric proteome analysis with C-terminal tags (MPACT). After C-terminal labeling of proteins, the labeled proteins are hydrolyzed and C-terminal peptides recovered, e.g., using streptavidin-agarose. Biotin is depicted by "*". Note that only one peptide is recovered per parent protein.

The ability to label and recover C-terminal amino acids provides a straightforward way to perform proteome analysis (FIG. 4). In this method protein mixtures are labeled on their C-termini with a label comprising an affinity marker, e.g., biotin, and then digested with a specific protease to generate short peptides. The C-terminal peptides are selectively recovered using a ligand for the affinity marker, e.g., streptavidin-agarose, and their masses determined by liquid chromatography-coupled electrospray ionization (LC-ESI) MS. To correlate the peptide mass with the protein from which they were derived, the molecular mass of C-terminal peptides, in most cases, can be used uniquely to identify the protein from which the peptide was derived. Thus, a 2337.82 Da peptide is uniquely associated with catalase. These molecular masses can be calculated from the amino acid sequence of each protein identified in the genome sequencing project of that organism.

The size distribution and overlap of labels useful in the methods of the invention was tested using the yeast genomic sequence obtained from GenBank. A computer simulation of a proteolytic digestion by endoprotease Glu-C was generated. Following a virtual digest of the yeast proteome with this protease, 63.5% of proteins produces C-terminal peptides of appropriate size for high resolution (6-15 residues in length), unambiguous identification by ESI/MS. Use of endoprotease Glu-C in one digest followed by endoprotease Arg-C in the next digest results in 85.7% of the proteome producing MPACT tags appropriate for identification by ESI-MS. Typically, proteins that will produce a peptide suitable for MS analysis will be known prior to MS by inspection of the genome sequence.

MPACT provides a major advance over other MS-based studies of complex mixtures. By limiting analysis of a protein mixture to its C-terminal peptides, a yeast-derived lysate, which typically contains 6,000 proteins, will produce 344,000 tryptic peptides (Gygi et al., 1999), but will be simplified to a maximum of about 6,000 distinct peptides by MPACT. Identification of these peptides is thus powerfully constrained by the C-terminal origin of these peptides. Because MPACT produces one peptide per protein, it provides the most complete simplification of complex mixtures for proteome analysis. Also, because peptides rather than proteins are analyzed by MPACT, substantially more starting material can be used for preparing tagged C-terminal peptides than can be used for 2D-electrophoresis or other techniques that have been used for proteomics.

To avoid the simultaneous modification of carboxyl groups in glutamic and aspartic residues along with the C-terminus of proteins, a transpeptidase, CPY, an enzyme which binds to the C-termini of proteins as part of its catalytic activity, was employed. CPY is a C-terminal exopeptidase that hydrolyzes C-terminal amino acids using water as a nucleophile. CPY is also a C-terminal esterase, hydrolyzing C-terminal esters in proteins whose carboxy-terminus has been esterified (Hayashi et al., 1975). The exopeptidase activity is inhibited above pH 8, while the esterase activity is unaffected (Hayashi et al., 1975).

Surprisingly, the exopeptidase activity of CPY can utilize amino acids as nucleophiles in place of water (Beme et al., 1990). Thus, in the presence of high concentrations of, for example, alanine, the alpha-amino group of alanine can attack the peptide bond between the penultimate and last amino acid, resulting in a replacement of the last amino acid with alanine. This reaction occurs in competition with water, and only a small fraction of proteins undergo the alanine-mediated reaction, while most undergo the water-mediated reaction (Buckler et al., 1993).

As the CPY-dependent amino acid incorporation reaction exists in competition with water, the C-terminal residue can be hydrolyzed several times before an amino acid is incorporated. To test if biotin-containing nucleophiles could be used as an alternative nucleophile in the esterase reaction of CPY, bovine serum albumin (BSA) was derivatized such that all the carboxyl groups, including the C-terminal carboxyl group, were methyl esterified to generate a substrate for the esterase reaction. The nucleophile that was used was biocytin, a derivative of biotin found in nature. The methyl esterified protein was incubated with CPY and several biocytin analogs, including biocytin (biocytin-OH), a biocytin methyl ester (biocytin-Ome), and a carboxyamidated biocytin (biocytin-NH2). CPY was found to label methyl esterified BSA (BSA-ME), and that the carboxyamidated derivative, biocytin-NH2, is a much more efficient substrate than the other biocytin derivatives in the CPY-dependent biotinylation reaction (FIG. 5).

To enhance the access of the C-terminus of the proteins to CPY, proteins are initially denatured in the presence of SDS, followed by the addition of Triton X-100. CPY is added following the addition of Triton X-100. The presence of this nondenaturing detergent sequesters free SDS monomers and prevents SDS from inhibiting the enzyme.

Figure 5A:
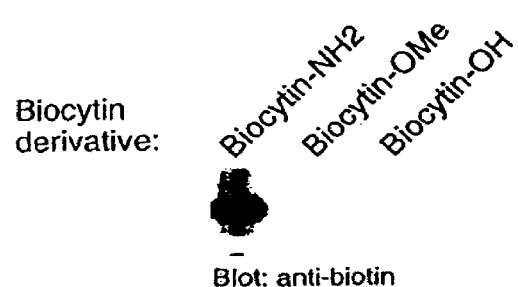
FIG. 5. Biotinylation of proteins by CPY and biocytin-$NH_2$. A) Biotinylation of BSA-methyl ester was tested by incubation of CPY and various biocytin derivatives. Biotinylated BSA was detected by anti-biotin Western blot. Biocytin-$NH_2$ was a preferred substrate for biotinylation. B) BSA-ME is a substrate for CPY-dependent labeling. BSA prepared with methanol and HCl is methyl esterified, and this is the only preparation that is labeled by Western blot. C) The methyl ester is hydrolyzed by base for the indicated times prior to being subjected to CPY-dependent labeling. Hydrolysis of the ester reduced the ability of BSA to serve as a substrate. D) Biotinylation of various GST-amino acid fusion protein methyl esters. Biotinylation of the indicated GST-fusions was performed and protein were subjected to anti-biotin Western blotting. CPY was able to biotinylate each fusion protein, indicating that all proteins regardless of the C-terminal amino acid are likely to be substrates for CPY-mediated ligation.
Figure 5B:
Figure 5C:
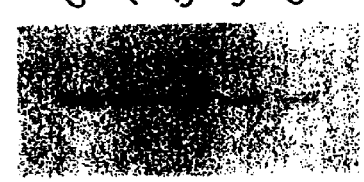
Figure 5D:

The reaction involves the esterase activity of CPY, as BSA-ME, and not unmodified BSA, was the substrate for the reaction (FIG. 5B). Furthermore, removal of the methyl ester by gentle base hydrolysis prevented the incorporation of biotin (FIG. 5C). Thus, CPY is capable of biotinylating BSA-ME. Trypsinolysis, and purification of C-terminal peptides using streptavidin-agarose, followed by MALDI-MS based detection of BSA-labeled protein is consistent with a C-terminal labeling reaction.

To determine if CPY was capable of modifying a variety of proteins, regardless of the C-terminal amino acid, twenty glutathione-S-transferase (GST) fusions containing GST followed by each of the twenty common amino acids were prepared, and it was found that each was a substrate for CPY (FIG. 5D), indicating that CPY could label a variety of proteins, and each C-terminal amino acid could be used in a labeling reaction.

In other experiments, enzyme, protein substrate, and nucleophile concentrations for the CPY-dependent labeling reaction were altered. Identical results were obtained for a variety of other selected proteins, including superoxide dismutase, glyceraldehydes-1-3-phosphate dehydrogenase catalase, and calmodulin. Additionally, whole rat liver lysate and yeast mitochondrial preparations were similarly biotinylated by CPY in a biocytin-NH2-dependent fashion.

EXAMPLE 5

Biotinamidoethyl Dithiocysteineamide (BADTC)

Figure 6A:
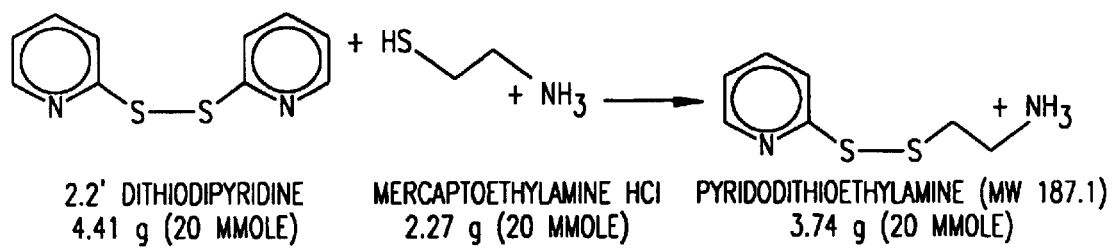
FIGS. 6A through 6C illustrate a synthetic strategy for biotinamidoethyl dithiocysteineamide and its similarity to biocytin-$NH_2$.
Figure 6B:
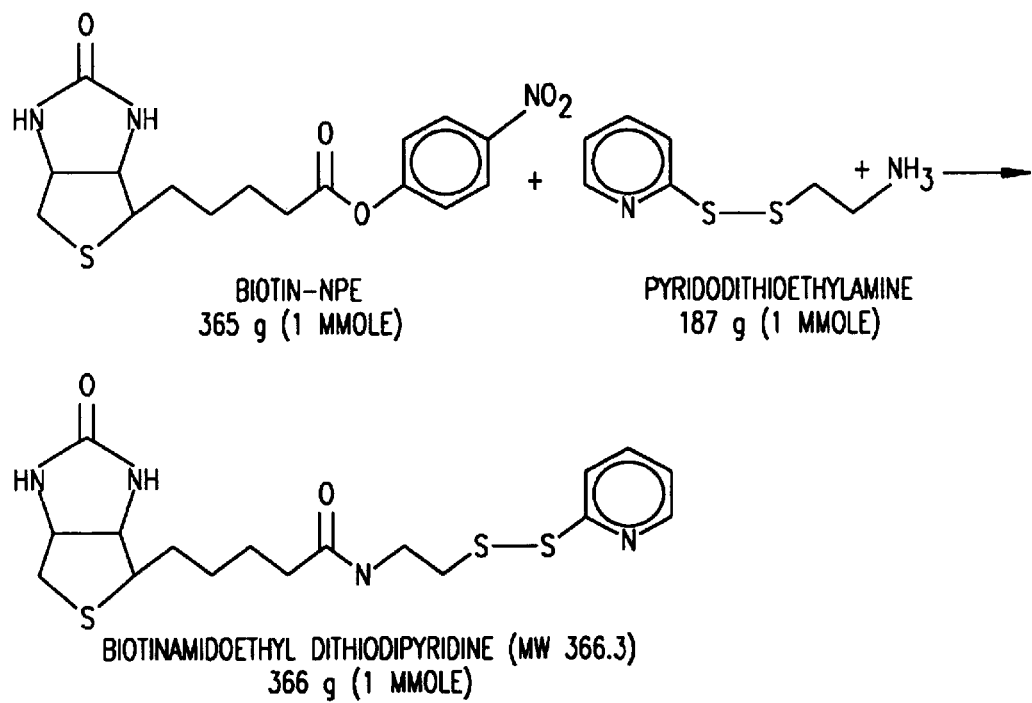
Figure 6C:
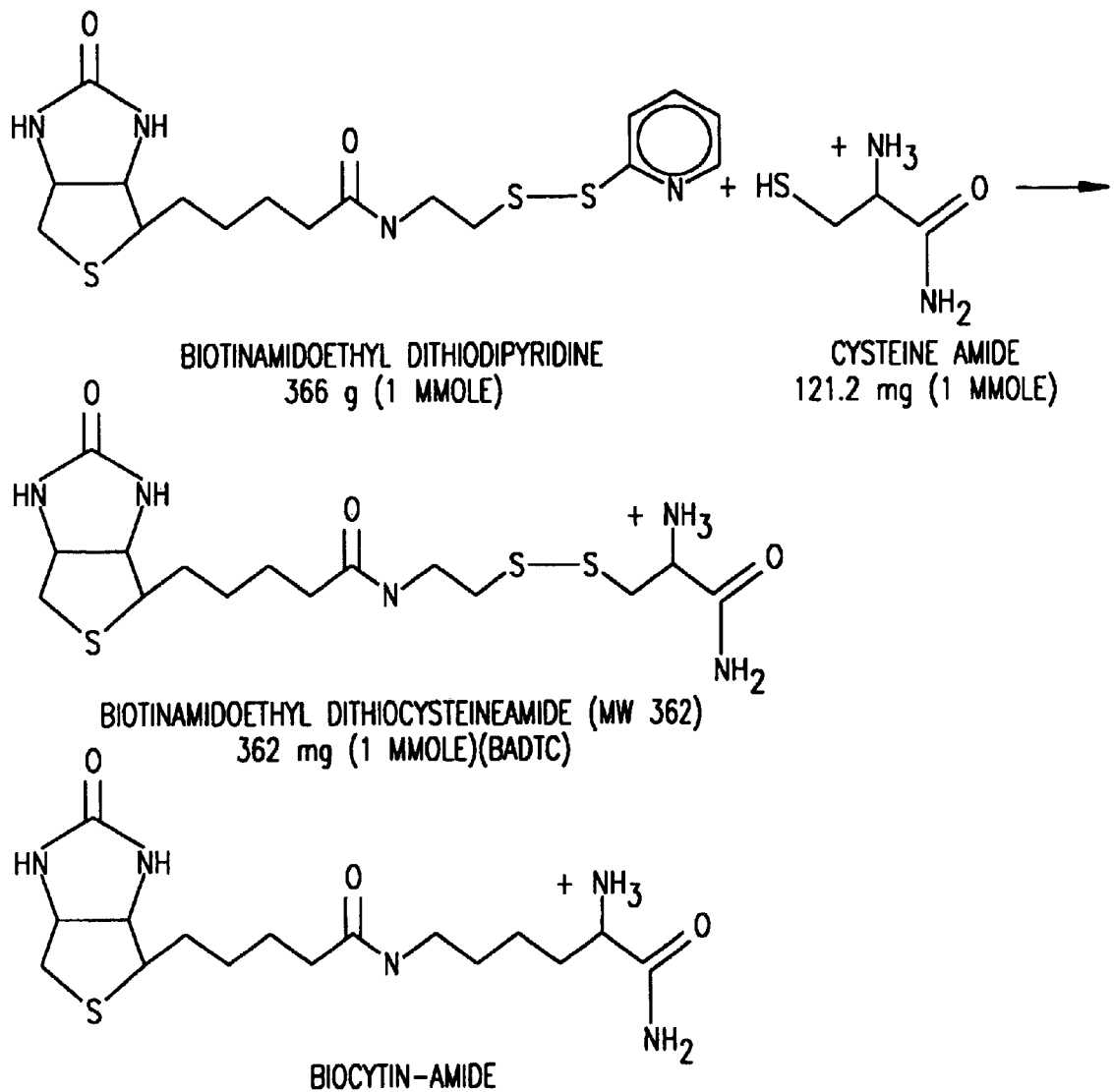

As described above, prior to MALDI-MS, peptides were purified on streptavidin-agarose and eluted with guanidine HCl. The peptides were then desalted using reverse phase chromatography. The unusually high affinity of the biotin-streptavidin interaction ($k_D$ of about $10^{-15}$) resulted in less than optimal elution of the peptides from the streptavidin-agarose. To enhance the recovery of C-terminal peptides, a biotinylated amino acid, biotinamidoethyl dithiocysteineamide (BADTC), was prepared (FIG. 6). BADTC is similar to biotin-$NH_2$ in chemical structure, except that BADTC has a disulfide bond, which can be reduced with 2-mercaptoethanol (2-ME). BADTC-labeled peptides were purified on streptavidin-agarose and then eluted from the resin with 2-ME (a mild elution protocol). The eluted peptides each contain a C-terminal cysteineamide, however, biotin remains on the streptavidin-agarose. 2-ME is removed by lyophilization prior to ESI-MS. To confirm that BADTC-labeling is compatible with a variety of proteins as well as GST fusions containing each of the twenty common C-terminal amino acids at its C-terminus, various fusions are prepared in E. coli in a manner identical to the GST-X experiments described in Example 4 and analyzed.

Analogs of BADTC may be better substrates for CPY ligation. In particular, the mercaptoalkylamine component of BADTC can be modified by using various mercaptoalkylamines with different numbers of methylene groups. The role of distance between the alpha-carbon and the disulfide may be evaluated using homocysteine, which has an additional methylene group between the alpha-carbon and the sulfur atom, rather than cysteine. Structures are confirmed using 1 H-NMR and mass spectrometry.

Figure 7:
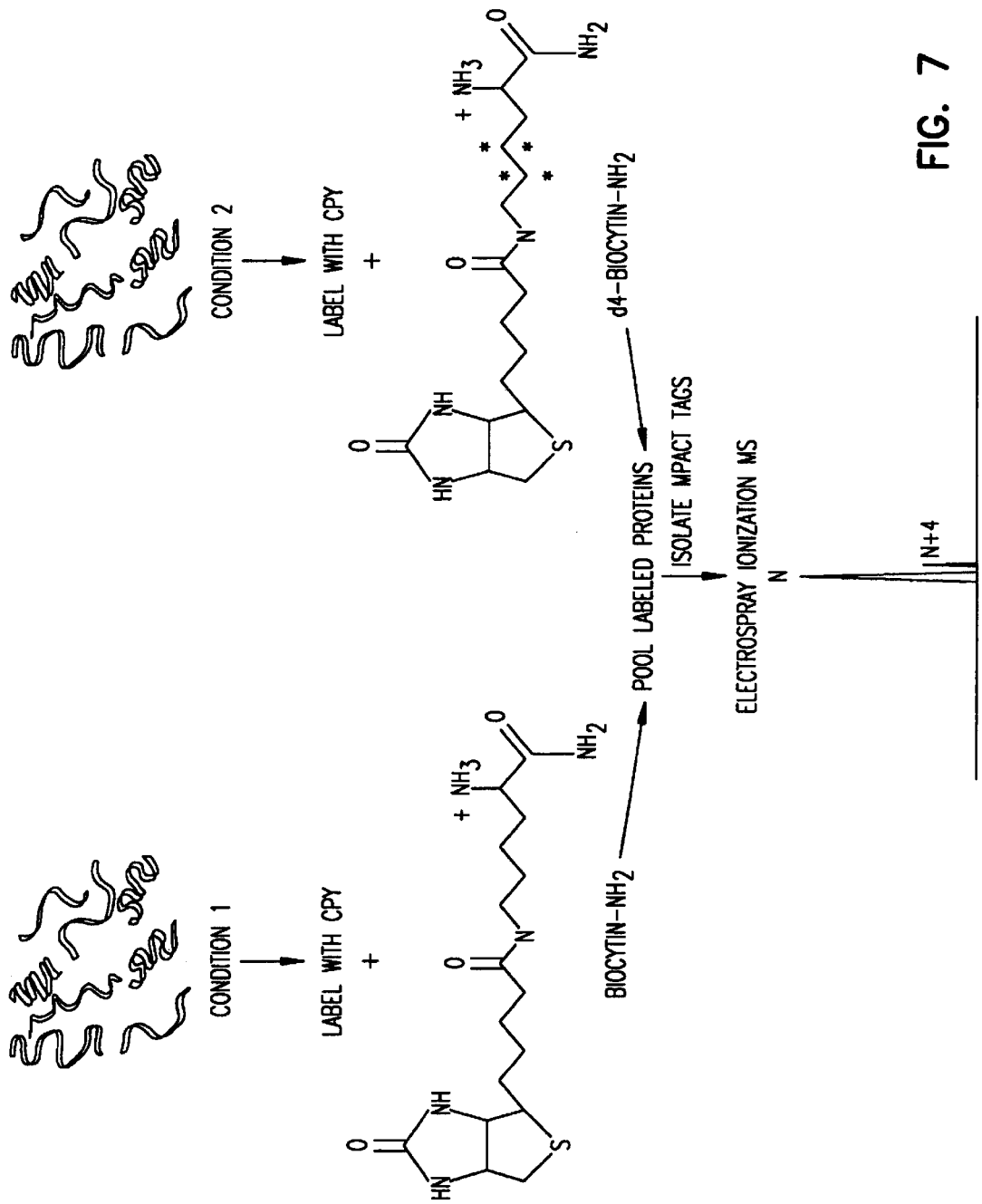
FIG. 7 shows quantitative MPACT. The use of deuterated (depicted with stars) biotin-containing amino acids in the CPY-dependent labeling reaction results in peptide mixtures that have MPACT tags whose molecular mass is increased by the number of deuterium atoms in the biotin nucleophile. Identical peptides coelute and the relative amounts of each parent protein can be inferred by the relative signals produced by the two peptides.

In order to perform comparative MPACT (FIG. 7), a strategy in MS involving the use of labels comprising non-natural isotopes such as deuterated tags, is employed. $d_3$-BADTC, containing three deuterium ions in the cysteineamide moiety of BADTC, is synthesized, using commercially available $d_3$-cysteine. To compare two samples, proteins from one sample, e.g., condition-1, are labeled with BADTC, while proteins from sample 2, e.g., condition-2, are labeled with $d_3$-BADTC (FIG. 7). The samples are pooled and trypsinized together, and peptides comprising the affinity marker are recovered, e.g., using avidin-agarose and 2-ME, and simultaneously subjected to LC-ESI MS. Because each peptide has either a cysteineamide or a $d_3$-cysteineamide, the MS spectrum will contain a series of doublets separated by 3 atomic mass units; the lighter peak corresponding to a peptide derived from condition-1, and the heavier peptide corresponding to condition-2. The relative expression level is determined by the ratio of the signal intensity between the two peaks.

As an alternative approach, a PCB-NHS ester is condensed with $^{13}C_4$- or $d_4$-lysinamide to generate a photocleavable lysinamide non-natural isotope containing affinity marker (PLICAT), and purified by HPLC. PLICAT synthesis is verified by NMR and MS. Although structurally longer than biocytin-$NH_2$, photocleavage of PLICAT results in the incorporation of a C-terminal lysinamide, imparting an additional positive charge to the peptide fragment that, in some cases, facilitates detection after CID. PLICAT derivatives using lysinamide derivatives are also prepared.

MPACT can thus be used to examine more complex proteomes, including whole yeast, and human biological specimens, including physiological fluids include CSF and serum, as well as other extracellular samples, and subcellular, e.g., membrane, fractions.

REFERENCES

Adams et al., *Science*, 287:2185 (2000).
Alexandre et al., *FEBS Lett.*, 498:98 (2001).
Anderson et al., *Electrophoresis*, 18:533 (1997).
Beme et al., *J. Biol. Chem.*, 265:19551 (1990).
Brand, *Cancer J.*, 7:287 (2001).
Buckler et al., *Anal. Biochem.* 209:20 (1993).
Endrizzi et al., *Biochemistry*, 33:11106 (1994).
Futcher et al., *Mol. Cell. Biol.*, 19:7357 (1999).
Gygi et al., *Mol. Cell. Biol.*, 19:1720 (1999).
Gygi et al., *Nat. Biotechnol.*, 17:994 (1999).
Haurie et al., *J. Biol. Chem.*, 276:76 (2001).
Hayashi et al., *J. Biochem.* (Tokyo), 77:69 (1975).
Jaffrey et al., *Nat. Cell. Biol.*, 3:193 (2001).
Koller, *Exp. Neurol.*, 144:24 (1997).
Mewes et al., *Nature*, 387:7 (1997).
Mortensen et al., *Biochemistry*, 33:508 (1994).
O'Farrel et al., *J. Biol. Chem.*, 250:4007 (1975).
Olesen et al., *Biochemistry*, 36:12235 (1997).
Porath et al., *Nature*, 258:598 (1992).
The *C. elegans* Sequencing Consortium, *Science*, 282:2012 (1998).
Sechi et al., *Anal. Chem.*, 70:5150 (1998).
Sorenson et al., *Protein Sci.*, 6:2227 (1997).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method of separating peptides in a mixture of isolated C-terminally labeled peptides, comprising:
   a) providing a hydrosylate comprising a mixture of C-terminally labeled distinct peptides obtained by subjecting a plurality of C-terminally labeled distinct proteins to hydrolysis, wherein the label comprises an affinity marker, and wherein the C-terminally labeled distinct proteins are prepared by contacting a sample comprising a plurality of distinct proteins with the label and a transpeptidase that catalyzes the transfer of one molecule of the affinity marker to the C-terminus of the plurality of distinct proteins in the sample under conditions that favor the additive reaction over the exopeptidase reaction;
   b) contacting the hydrosylate with a ligand for the affinity marker so as to form a complex, thereby isolating the C-terminally labeled distinct peptides;
   c) disrupting the complex formed by the binding of the ligand to the affinity marker to yield purified C-terminally labeled distinct peptides; and
   d) separating the purified C-terminally labeled distinct peptides by mass spectrometry.

2. The method of claim 1 wherein the affinity marker is biotin, biocytin, a peptide antigen, polyhistidine, dinitrophenol, an oligonucleotide or a peptide nucleic acid.

3. The method of claim 1 wherein the label is photocleavable.

4. The method of claim 1 wherein the transpeptidase is carboxypeptidase Y.

5. The method of claim 1 wherein the label further comprises a non-natural isotope.

6. The method of claim 1 wherein the plurality of distinct proteins in the sample are esterified prior to contact with the transpeptidase.

7. The method of claim 1 wherein the ligand is streptavidin, avidin, neutravidin, or monomeric avidin.

8. The method of claim 1 wherein the ligand is coupled to a solid support.

9. The method of claim 1 wherein the hydrolysate is prepared by contacting the plurality of C-terminally labeled distinct proteins with a protease.

10. The method of claim 9 wherein the protease is trypsin, chymotrypsin, pepsin, papain, proteinase K, calpain, subtilisin endoprotease Glu-C, or endoprotease Arg-C.

11. The method of claim 1 wherein the hydrolysate is prepared by chemical hydrolysis.

12. The method of claim 11 wherein the hydrosylate is prepared by contacting the plurality of C-terminally labeled proteins with cyanogen bromide.

13. The method of claim 1 wherein the plurality of distinct proteins are denatured prior to contact with the transpeptidase.

14. The method of claim 13 wherein the plurality of distinct proteins are denatured with SDS.

15. The method of claim 1 further comprising, prior to separating the purified C-terminally labeled distinct peptides by mass spectrometry, fractionating the purified C-terminally labeled distinct peptides.

16. The method of claim 15 wherein liquid chromatography, ion exchange chromatography or capillary electrophoresis is employed to fractionate the purified C-terminally labeled distinct peptides.

17. The method of claim 1 further comprising identifying one or more of the separated C-terminally labeled distinct peptides.

18. The method of claim 1 further comprising treating the isolated C-terminally labeled distinct peptides with an agent so as to yield C-terminal peptides which lack the affinity marker.

19. The method of claim 18 further comprising purifying the C-terminal peptides which lack the affinity marker.

20. The method of claim 19 further comprising separating the purified C-terminal peptides which lack the affinity marker by mass spectrometry.

21. The method of claim 20 further comprising, prior to separating the purified C-terminal peptides which lack the affinity marker by mass spectrometry, fractionating the purified C-terminal peptides which lack the affinity marker.

22. The method of claim 21 wherein liquid chromatography, ion exchange chromatography or capillary electrophoresis is employed to fractionate the purified C-terminally labeled peptides which lack the affinity marker.

23. The method of claim 20 further comprising identifying one or more of the separated C-terminal peptides which lack the affinity marker.

24. The method of claim 1 wherein the sample is a cellular sample.

25. The method of claim 1 wherein the sample is a physiological fluid sample.

26. The method of claim 25 wherein the sample is serum, plasma, urine or cerebrospinal fluid.

27. The method of claim 1 wherein the sample is a subcellular fraction.

28. A method for identifying distinct proteins in a sample comprising a plurality of distinct proteins, comprising:
   a) contacting a hydrosylate comprising a mixture of C-terminally labeled distinct peptides obtained by subjecting a plurality of C-terminally labeled distinct proteins comprising an affinity marker to hydrolysis, with a ligand for the affinity marker so as to isolate C-terminally labeled distinct peptides, wherein the C-terminally labeled distinct proteins are prepared by contacting a sample comprising a plurality of distinct proteins with a label comprising the affinity marker and a transpeptidase that catalyzes the transfer of one molecule of the affinity marker to the C-terminus of the plurality of distinct proteins in the sample under conditions that favor the additive reaction over the exopeptidase reaction;
   b) disrupting the complex formed by the binding of the ligand to the affinity marker to yield purified C-terminally labeled distinct peptides;
   c) separating the purified C-terminally labeled distinct peptides by mass spectrometry; and
   d) identifying at least one separated peptide, thereby identifying at least one protein in the sample.

29. A method for identifying distinct proteins in a sample comprising a plurality of distinct proteins, comprising:
   a) contacting a hydrosylate comprising a mixture of C-terminally labeled distinct peptides obtained by subjecting a plurality of C-terminally labeled distinct proteins comprising an affinity marker to hydrolysis with a protease, with a ligand for the affinity marker so as to isolate C-terminally labeled distinct peptides, wherein the C-terminally labeled distinct proteins are prepared by contacting a sample comprising a plurality of distinct proteins with a label comprising the affinity marker and a transpeptidase that catalyzes the transfer of one molecule of the affinity marker to the C-terminus of the plurality of distinct proteins in the sample under conditions that favor the additive reaction over the peptidase reaction;
   b) treating the isolated C-terminally labeled distinct peptides with an agent so as to yield purified C-terminal distinct peptides which lack the affinity marker;
   c) separating the purified C-terminal distinct peptides by mass spectrometry; and
   d) identifying at least one separated peptide, thereby identifying at least one protein in the sample.

30. A method for comparing the amount or level of one or more proteins in at least 2 samples, comprising:
   a) providing a first sample comprising a plurality of C-terminally labeled distinct proteins and a second sample comprising a plurality of C-terminally labeled distinct proteins, wherein the label for the first sample comprises an affinity marker but not a non-natural isotope, wherein the label for the second sample comprises the affinity marker and a non-natural isotope, wherein the C-terminally labeled distinct proteins in the first sample are prepared by contacting the first sample with the label comprising the affinity marker but not a non-natural isotope with a transpeptidase that catalyzes the transfer of one molecule of the affinity marker to the C-terminus of a plurality of distinct proteins under conditions that favor the additive reaction over the exopeptidase reaction, and wherein the C-terminally labeled distinct proteins in the second sample are prepared by contacting the second sample with the label comprising the affinity marker and a non-natural isotope with the transpeptidase;

b) hydrolysing the C-terminally labeled distinct proteins in the first and the second sample so as to form a first hydrosylate from the first sample and a second hydrosylate from the second sample;

c) contacting the hydrosylate first and second hydrosylates with a ligand for the affinity marker so as to isolate C-terminally labeled distinct peptides;

d) purifying the isolated C-terminally labeled distinct peptides from each hydrosylate by disrupting the interaction between the ligand and the affinity marker;

e) separating the purified C-terminally labeled distinct peptides by mass spectrometry; and f) comparing the amount or level of at least one separated C-terminally labeled peptide from the first sample to the amount or level of the corresponding separated C-terminally labeled peptide from the second sample.

31. A method for comparing the amount or level of one or more proteins in at least two samples, comprising:

a) providing a first sample comprising a plurality of C-terminally labeled distinct proteins and a second sample comprising a plurality of C-terminally labeled distinct proteins, wherein the label for the first sample comprises an affinity marker but not a non-natural isotope, wherein the label for the second sample comprises the affinity marker and a non-natural isotope, wherein the C-terminally labeled distinct proteins in the first sample are prepared by contacting the first sample with the label comprising the affinity marker but not a non-natural isotope with a transpeptidase that catalyzes the transfer of one molecule of the affinity marker to the C-terminus of a plurality of distinct proteins under conditions that favor the additive reaction over the exopeptidase reaction, and wherein the C-terminally labeled distinct proteins in the second sample are prepared by contacting the second sample with the label comprising the affinity marker and a non-natural isotope with the transpeptidase;

b) hydrolysing the C-terminally labeled distinct proteins in the first and the second sample so as to form a first hydrosylate from the first sample and a second hydrosylate from the second sample;

c) contacting the first and second hydrosylates with a ligand for the affinity marker so as to isolate C-terminally labeled peptides from each hydrosylate;

d) treating the isolated C-terminally labeled distinct peptides from each hydrosylate with an agent so as to yield C-terminal peptides which lack the affinity marker;

e) separating the C-terminal peptides which lack the affinity mark by mass spectrometry; and f) comparing the amount or level of at least one separated C-terminally labeled peptide from the first sample to the amount or level of the corresponding separated C-terminally labeled peptide from the second sample.

32. The method of claim 30 or 31 wherein the samples are mixed together prior to step f).

33. The method of claim 1, 28, 29, 30, or 31 wherein the contacting of the sample comprising a plurality of distinct proteins with a label comprising the affinity marker and a transpeptidase is at a pH above 8.

* * * * *

UNITED STATES PATENT AND TRADEMARK OFFICE
CERTIFICATE OF CORRECTION

PATENT NO. : 7,674,766 B2  Page 1 of 1
APPLICATION NO. : 11/057082
DATED : March 9, 2010
INVENTOR(S) : Samie R. Jaffrey It is certified that error appears in the above-identified patent and that said Letters Patent is hereby corrected as shown below:

On the title page, item (56), under "Other Publications", in column 2, line 35, delete "Pan Dori," and insert -- Pandori, --, therefor.

In column 21, line 8, in Claim 30, after "the" delete "hydrosylate".

Signed and Sealed this

Eighteenth Day of May, 2010

David J. Kappos
*Director of the United States Patent and Trademark Office*